United States Patent [19]

Chang et al.

[11] Patent Number: 4,704,462

[45] Date of Patent: Nov. 3, 1987

[54] SUBSTITUTED 2,3,3A,6-TETRAHYDRO-6-OXOBENZOFURAN DERIVATIVE USEFUL AS PAF ANTAGONIST

[75] Inventors: Michael N. Chang, Westfield; San-Bao Hwang, Scotch Plains; Mitree M. Ponpipom, Branchburg; Robert L. Bugianesi, Colonia, all of N.J.

[73] Assignee: Merck & Co., Inc., Rahway, N.J.

[21] Appl. No.: 768,009

[22] Filed: Aug. 22, 1985

[51] Int. Cl.$^4$ ........................................... C07D 307/83
[52] U.S. Cl. .................... 549/466; 544/182; 544/376; 546/196; 546/269; 548/252; 548/336; 549/60; 549/414
[58] Field of Search ........................................ 549/466

[56] References Cited

U.S. PATENT DOCUMENTS 4,540,709  9/1985  Chang et al. ................... 549/466

OTHER PUBLICATIONS

K. Matsui et al., Agr. Biol. Chem., 40, 1045, 1113 (1976).
G. Buchi et al., J. Chem. Soc., 99, No. 24, pp. 8073–8075 (1977).
Y. Shizuri et al., Tet. Letters, 24, No. 45, pp. 5011–5012 (1983).
O. A. Lima et al., Chem. Abstrs., 77:101311x (1972).
J. B. Fernandes et al., Chem. Abstrs. 86:13793m (1977).
C. J. Aiba et al., Chem. Abstrs. 87:151909a (1977).
R. Braz Filho et al., Chem. Abstrs. 93:146271f (1980).

Primary Examiner—Henry R. Jiles
Assistant Examiner—Bernard I. Dentz
Attorney, Agent, or Firm—Theresa Y. Cheng; Michael C. Sudol

[57] ABSTRACT

Substituted 2,3,3a,6-tetrahydro-6-oxobenzofuran derivatives have been prepared. These neolignans are found to have potent and specific PAF (Platelet-Activating-Factor) antagonistic activities and thereby useful in the treatment of various diseases or disorders mediated by PAF, for example, pain, fever, inflammation, cardiovascular disorder, asthma, lung edema, allergic disorders, skin diseases, psoriasis, toxic shock syndrome and adult respiratory distress syndrome.

1 Claim, No Drawings

SUBSTITUTED 2,3,3A,6-TETRAHYDRO-6-OXOBENZOFURAN DERIVATIVE USEFUL AS PAF ANTAGONIST

BACKGROUND OF THE INVENTION

Platelet-activating factor (PAF) has recently been identified as an acetyl glyceryl ether phosphorylcholine (AGEPC), i.e., 1-O-hexadecyl/octadecyl-2-O-acetyl-sn-glycero-3-phosphorylcholine (Hanahan, D. S. et al., *J. Biol. Chem.*, 255: 5514, 1980). It is a potent lipid mediator of inflammation and anaphylaxis and is produced by stimulated basophils, neutrophils, platelets, macrophages, endothelial cells, and IgE-sensitized bone marrow mast cells. PAF exerts a myriad of biological actions. It induces smooth-muscle contraction, aggregation, chemotaxis, and degranulation of neutrophil and heightened metabolic activity of macrophages in vitro. It also reduces coronary blood flow and contractile force of isolated guinea pig heart, leading to cardiac anaphylaxis. In various animal models, PAF induces bronchoconstriction, hyperalgesia, hypotension, neutropenia, thrombocytopenia, increased cutaneous vascular permeability, increased hematocrit, and lysosomal enzyme secretion. In man, intradermal injection of PAF at 0.1 μg per site elicits a biphasic inflammatory response, which is potentiated by prostaglandin $E_2$. Thus, PAF has been linked to various biologic activities and pathways making it one of the important mediators responsible for a variety of physiological process which are known to be associated with a large group of diseases, for example, inflammatory diseases, cardiovascular disorders, asthma, lung edema, endotoxin shock syndrome, and adult respiratory distress syndrome.

The compounds of the present invention are potent and specific PAF-antagonists. They belong to the class of neolignan compounds related to piperenone, a known insect antifeeding substance, and 5-allyl-2-(3,4-dimethoxyphenyl)-3a,α-methoxy-3-methyl-2,3,3a,6-tetrahydro-6-oxobenzofuran, the subject matter of co-pending application Ser. No. 541,806, filed Oct. 13, 1983 now U.S. Pat. No. 4,540,709. Both piperenone and the 5-allyl compound mentioned above were isolated from the Chinese herbal plant *Piper futokadzsura* Sieb. See K. Matsui et al., *Agr. Biol. Chem.* 40, 1045 (1976); ibid, 40, 1113 (1976); and Matsui et al., *Tetrahedron Letters* 24, 1905 (1975). Although the plant has been used in Chinese herbal medicine for the treatment of arthritic conditions, no one had successfully isolated nor identified the active substance until our work on the 5-allyl compound and the compounds of the present invention. We found these compounds to be potent and specific PAF-antagonists useful not only in the treatment of arthritic conditions but also for other diseases including asthma, hypertension, lung-edema, endotoxin shock syndrome, adult distress syndrome and the like.

Accordingly, it is the object of the present invention to provide a class of novel compounds as specific PAF-antagonists.

Another object of this invention is to provide processes for the preparation of these PAF-antagonists.

A further object of this invention is to provide a pharmaceutically acceptable composition containing these novel compounds as the active ingredient for the treatment of diseases which are subject to the mediation of PAF.

Still a further object of this invention is to provide a method of treatment comprising the administration of a therapeutically sufficient amount of one or more of the PAF-antagonists to a patient suffering from various skeletal-muscular disorders including but not limited to inflammation, e.g., osteoarthritis, rheumatoid arthritis and gout; allergic disorders; hypertension; cardiovascular disorder; asthma; lung edema; skin diseases; psoriasis; endotoxin shock syndrome; or adult respiratory distress syndrome.

DETAILED DESCRIPTION OF THE INVENTION

A. Scope of the Invention

This invention relates to the specific PAF-antagonists of formula:

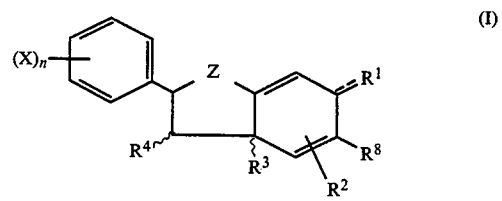

(I)

wherein
$R^1$ is
(1) when it is joined to the ring by a double bond, O, S, $CR^5R^6$, $NR^5$ or $NOR^5$ where $R^5$ and $R^6$ independently represent H, loweralkyl, haloloweralkyl, loweralkenyl, aryl or aralkyl as defined below; or
(2) when it is joined to the ring by a single bond, $SR^5$, $SOR^5$, $SO_2R^5$, $NR^5R^6$, or $OR^7$ wherein $R^7$ represents $R^5$, $COR^5$, $COOR^5$, $CSR^5$ or $COSR^5$;
$R^2$ is
  (a) loweralkyl especially $C_{1-6}$alkyl such as methyl, n-propyl, i-propyl, t-butyl, cyclopropyl, n-hexyl, cyclopentyl or cyclohexyl;
  (b) loweralkenyl especially $C_{1-6}$alkenyl such as vinyl, allyl, —$CH_2CH$=$CH$—$CH_3$ or —$CH_2$—$CH_2CH$=$CHCH_2CH_3$; or
  (c) loweralkoxy especially $C_{1-6}$alkoxy such as methoxy, ethoxy or propoxy;
  (d) lower alkynyl especially $C_{1-6}$ alkynyl, e.g. —$CH_2$—$C$≡$CH$, —$C$≡$C$—$CH_3$ and —$CH_2$—$C$≡$C$—$CH_3$;
  (e) aralkyl especially aryl loweralkyl such as benzyl or substituted benzyl, e.g., p-methoxybenzyl, m,p-dinitrobenzyl o,p-difluorobenzyl or p-methylbenzyl;
  (f) haloloweralkyl especially $CF_3$;
$R^3$ is
  (a) loweralkyl especially $C_{1-6}$alkyl;
  (b) aryl especially phenyl or substituted phenyl such as p-methoxyphenyl, 2,4-dichlorophenyl, p-methylphenyl or the like; or
  (c) loweralkenyl especially $C_{1-6}$ alkenyl;
  (d) $OR^5$ where $R^5$ is as previously defined except that it cannot be $CH_3$;
  (e) O—CO—$R^5$;
  (f) $SR^5$;
  (g) $NR^5R^6$; or
  (h) haloloweralkyl;
$R^4$ is
  (a) loweralkyl especially $C_{1-6}$ alkyl;
  (b) lower alkenyl;
  (c) lower alkynyl;
  (d) hydrogen; or (e) aralkyl;
(f) hydroxy;
(g) alkoxy;
(h) halogen;
(i) azido;
(j) amino;
(k) alkylamino;
(l) dialkylamino;
(m) nitro;
(n) cyano; or
(o) thioalkyl;

X is
(1) H;
(2) loweralkyl especially $C_{1-6}$ alkyl such as methyl, ethyl, propyl, t-butyl, pentyl, benzyl, cyclopropyl, cyclopentyl or cyclohexyl;
(3) loweralkenyl especially $C_{2-6}$ alkenyl, for example, vinyl, allyl, and buten-2-yl;
(4) loweralkynyl especially $C_{2-6}$ alkynyl such as $-C\equiv CH$, $-CH_2C\equiv CH$, $-C\equiv C-CH_3$;
(5) aryl of 6 to 10 carbons especially phenyl or substituted phenyl of formula $Ar(X')_n$ wherein $X'$ independently is X, n is 1 to 5;
(6) aralkyl especially aryl loweralkyl such as benzyl or $Ar(X')_n$-loweralkyl;
(7) $R^5O-$;
(8) $R^5CO$;
(9) $R^5COO$;
(10) $R^5COS$;
(11) $R^5OCO$;
(12) $R^5SCO$;
(13) $R^5CONR^6$;
(14) $R^5NR^6CO$;
(15) $R^5R^6N$;
(16) $R^5S$;
(17) $R^5SO$;
(18) $R^5SO_2$;
(19) halo especially fluoro, chloro or bromo;
(20) $-O(CH_2)_mO-$ where m represents 1 or 2;
(21) $-(NH_2)C=NH$;
(22) $-CN$;
(23) $-NO_2$;
(24) $-(CH_2)_mOR^5$;
(25) $-(CH_2)_mCOOR^5$;
(26) heteroaryl or substituted heteroaryl of formula $Q_rX'$ where $Q_r$ is heteroaryl such as thienyl, furyl, pyridyl, pyrazinyl, pyrimidinyl, pyridazinyl, triazinyl, isoxazolyl, isothiazolyl pyrryl, imidazolyl, pyrazolyl, pyranyl, 2H-pyrryl, imidazolidinyl, imidazolinyl, pyrazolidinyl, pyrrolidinyl, pyrrolinyl, piperidyl, piperazinyl, morpholinyl, tetrazolyl, indolyl or the like; and X' is as previously defined; or
(27) halo loweralkyl especially $CF_3-$;

$R^8$ is
H n-propyl or allyl;

Z is
O, S, SO, $SO_2$, NH, $NR^6$ wherein $R^6$ is loweralkyl.

Preferably, the compounds of the present invention are of formula (II).

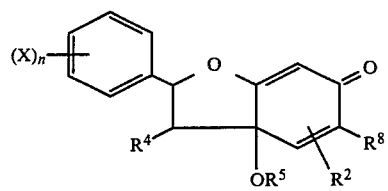
(II)

wherein $R^2$, $R^5$, $R^4$, X and n are as previously defined.

More preferably the compounds of the present invention are of formula (III)

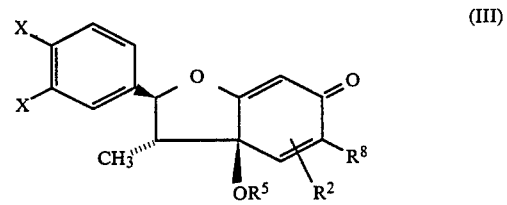
(III)

wherein $R^2$, $R^5$ and X are as previously defined.

The most preferred compounds of this invention are those having the following formula:

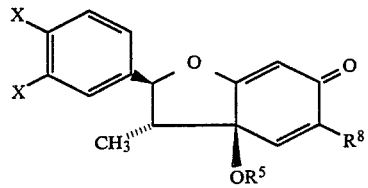

B. Preparation of the compounds within the scope of the invention

The novel compounds of the present invention can be prepared by the following representative processes:

Scheme (a)

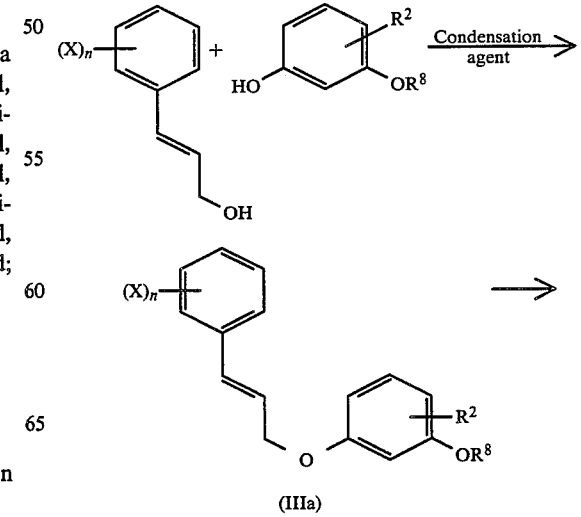
(IIIa)

-continued
Scheme (a)

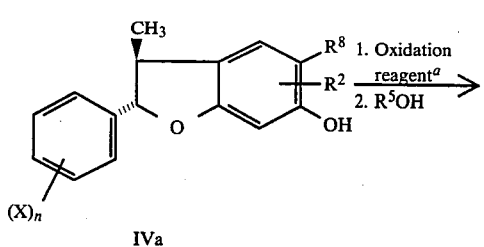

IVa

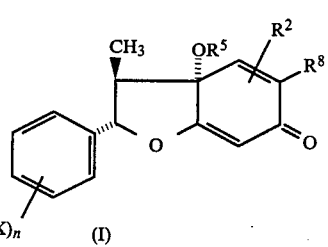

(I)

wherein $R^8$ is H or allyl; and the oxidants can be $Pb(OAc)_4$, $Pb(OBz)_4$, or $Tl(NO_3)_3 \cdot 3H_2O$ etc.

Scheme (b)

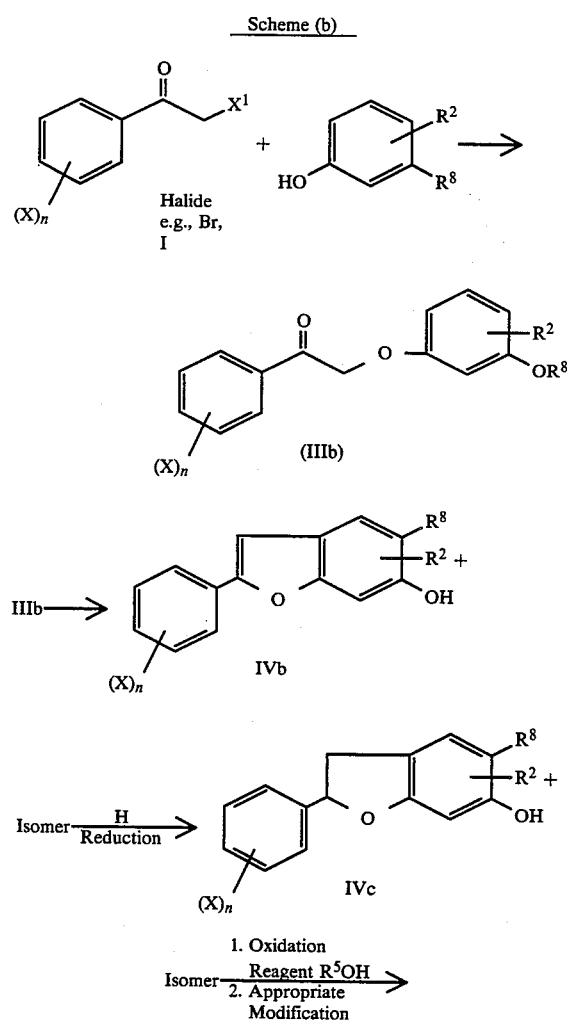

-continued
Scheme (b)

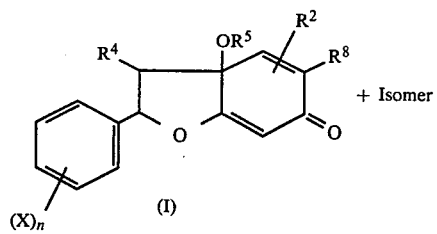

(I)

The starting materials of these processes are readily available. For example, the substituted m-hydroxyphenol is commercially available and the cinnamyl alcohol is easily prepared by reduction of the corresponding cinnamic acid.

The condensation to form the phenol ether (IIIa) or (IIIb) is conducted under dehydration conditions, e.g., the Mitsunobu conditions (Synthesis, 1, pabe 1 et seq., 1981), and dehydrobromination, respectively. The ring closure to produce the dihydrobenzofuran intermediate (IVa) or the benzofuran derivative (IVb) is carried out normally in a high boiling aprotic, neutral or basic solvent, e.g., diethylaniline, at about 150°–270° C., preferably, at about 220° to 250° C. When $R^8$ is allyl, the ring closure proceeds by way of a normal and an abnormal claisen rearrangement similar to that described by Schmid et al. in Helv. Chem. Acta., 55, page 1625 et seq., 1972. Finally, oxidation by lead tetraacetate or other mild oxidation reagents is employed to afford the compound of formula (I). For those compounds that may exist in optical isomers (d-, l-, or dl-form), resolution is accomplished by HPLC (high pressure liquid chromatography) using a chiral pak column or other conventional methods.

C. Utility of the compounds within the scope of the invention

This invention also relates to a method of treatment for patients (or mammalian animals rasied in the diary, meat, or fur industries or as pets) suffering from disorders or diseases which can be attributed to PAF as previously described, and more specifically, a method of treatment involving the administration of a compound of formula (I) as the active constituent.

Accordingly, the compounds of formula (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by the PAF, a compound of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or koalin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyxyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, the flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For typical use, creams, ointments, jellies, solutions or suspensions, etc., containing the anti-inflammatory agents are employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 25 to about 75 mg of the compound per kilogram of body weight per day (about 75 mg to about 3.75 gms per patient per day). Advantageously, from about 5 mg to about 50 mg per kilogram of body weight per daily dosage produces highly effective results (about 250 mg to about 2.5 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

D. Biological data supporting the utility of compounds within the scope of the invention The compounds of formula (I) have been found to be PAF inhibitors, as shown below in Table I, by a published bioassay. See. T. Y. Shen et al., *Proc. Nat. Acad. Sci.*, U.S.A., 82, 672 (1985); and S. B. Hwang et al., *Biochem.*, 22, 4756 (1983).

TABLE I

% Inhibition of PAF Receptor by the Compounds of Formula (I)

| X | n | $R^8$ | $R^2$ | $R^3$ | Dose (μM) | % Inhibition |
|---|---|---|---|---|---|---|
| 3,4-di-OCH$_3$ | — | —CH$_2$CH$_2$CH$_3$ | H | 3a, α-OCH$_3$ | 5 | 90–95 |
| | | | | | 1 | 83–89 |
| | | | | | 0.3 | 73–76 |
| | | | | | 0.1 | 58–59 |
| | | | | | 0.03 | 30–33 |
| 3,4-di-OCH$_3$ | — | —CH$_2$CH$_2$CH$_3$ | H | 3a, β-OCH$_3$ | 5 | 61 |
| | | | | | 1 | 31 |
| 3,4-di-OCH$_3$ | — | H | allyl | 3a, β-OCH$_3$ | 5 | 57 |
| | | | | | 1 | 26 |
| 3,4-di-OCH$_3$ | — | allyl | H | 3a, α-OC$_2$H$_5$ | 1 | 68 |
| | | | | | 0.3 | 42 |
| 3,4-di-OCH$_3$ | — | allyl | H | 3a, β-OC$_2$H$_5$ | 5 | 73 |
| | | | | | 1 | 45 |

The following examples serve to illustrate but are not intended to limit the scope of the present invention.

EXAMPLE 1

5-Allyl-2-(3,4-dimethoxyphenyl)-3-acetoxy-3-methyl-2,3,3a,6-tetra-hydro-6-oxobenzofuran Step A: Preparation of 3-Allyloxyphenol A solution of resorcinol (40 g, 0.4 mol) and allyl bromide (32 g, 0.26 mol) in acetone (500 ml) containing potassium carbonate (55 g, 0.4 mol) was heated, with stirring, under reflux for 10 hours. The mixture was filtered, and the filtrate was evaporated to dryness. The residue was purified by means of PrepPak 500/silica on a Waters Associates Prep LC/System 500 at 250 ml/min using hexane-ethyl acetate (8:1, v/v) as a liquid phase. 3-Allyloxyphenol was isolated as a colorless oil (20 g, 51% based on ally bromide); NMR (chloroform-d): δ4.78 (s, OH), 4.55 (d, J=5.5 Hz, CH$_2$CH=CH$_2$), 5.29–5.50 (m, CH$_2$CH=CH$_2$), 6.07 (m, CH$_2$CH=CH$_2$), 7.18 (t, J=8.5 Hz, H-5), 6.46–6.58 (m, remaining Ar—H).

Anal. Calc. for C$_9$H$_{10}$O$_2$: C, 71.98; H, 6.71. Found: C, 71.99; H, 6.63.

Step B: Preparation of Ethyl 3,4-dimethoxycinnamate

Carbethoxymethylene triphenylphosphorane (150 g, 0.3 mol) was added to a solution of 3,4-dimethoxybenzaldehyde (50 g, 0.3 mol) in dry dichloromethane (150 ml), and the mixture was stirred at room temperature overnight. The solution was concentrated to about 50 ml, and the precipitate was filtered off and washed with hexane-dichloromethane (4:1, v/v). The combined filtrates were evaporated to a residue, which was purified by silica gel chromatography using hexane-ethyl acetate (9:1, v/v) as the eluant. The title compound was isolated as a crystalline mass (65 g, 91%), m.p. 52°–53° C.

Anal. Calc. for C$_{13}$H$_{16}$O$_4$: C, 66.07; H, 6.83. Found: C, 66.18; H, 6.77.

Step C: Preparation of 3,4-Dimethoxycinnamyl Alcohol 3,4-Dimethoxycinnamyl alcohol was prepared by one of the following procedures:

(a) A solution of lithium aluminum hydride (0.02 mol) in diethyl ether (20 ml) was added dropwise to a solution of ethyl 3,4-dimethoxycinnamate (9.4 g, 0.04 mol) in diethyl ether (150 ml), and the mixture was heated under reflux for 1 hour. Water (15 ml) and 2.5N sodium hydroxide (5 ml) were added to the cooled solution, and the precipitate was filtered off and washed with ether. The combined filtrates were washed with water, dried, and evaporated to dryness. The crude product was put on a column of silica gel and eluted with hexane-ethyl acetate (1.5:1, v/v). 3,4-Dimethoxycinnamyl alcohol was isolated as a crystalline mass (5.0 g, 65%), m.p. 76°–76.5° C.

(b) A solution of lithium aluminum hydride (0.1 mol) in THF (100 ml) was added dropwise to a stirred suspension of 3,4-dimethoxycinnamic acid (41.6 g, 0.2 mol) in THF (150 ml) at room temperature. After the addition, the mixture was stirred for 2 hous, and the solution was evaporated in vacuo to a residue, which was partitioned between dichloromethane and aqueous sodium hydroxide. The organic layer was washed three times with water, dried, and evaporated to an oil. Crystallization from ethyl acetate-hexane gave 3,4-dimethoxycinnamyl alcohol (24 g, 62%), m.p. 76°–77° C.

Anal. Calc. for C$_{11}$H$_{14}$O$_3$: C, 68.00; H, 7.27. Found: C, 67.96; H, 7.15.

Step D: Preparation of 3,4-Dimethoxycinnamyl Allyloxyphenyl Ether

Diethyl azodicarboxylate (26.1 g, 0.15 mol) and triphenyl phosphine (39.3 g, 0.15 mol) were added to a solution of 3-allyloxyphenol (15 g, 0.1 mol) and 3,4-dimethoxycinnamyl alcohol (19.4 g, 0.1 mol) in THF (100 ml). The mixture was stirred at room temperature overnight, and ethyl ether was added. The precipitate was filtered off, and the filtrate was evaporated to a residue, which was purified by HPLC using hexane-ethyl acetate (4:1 v/v) as a liquid phase. 3,4-Dimethoxycinnamyl allyloxyphenyl ether was isolated as a crystalline mass (7.4 g, 23%), m.p. 60°–60.5° C.; NMR (CDCl$_3$): δ3.93, 3.94 (s, s, 2 OCH$_3$), 4.57 (d, t, J=5.5, 1.5, 1.5 Hz, CH$_2$CH=CH$_2$), 4.71 (d, d, J=6.0, 1.5 Hz, CH=CHCH$_2$), 5.28–5.50 (m, CH$_2$CH=CH$_2$), 6.10 (m, CH$_2$CH=CH$_2$), 6.26–6.40 (m, CH=CHCH$_2$), 6.56–7.28 (m, ArH).

Anal. Calc. for C$_{20}$H$_{22}$O$_4$: C, 73.60; H, 6.79. Found: C, 73.36; H, 6.81.

Step E: Preparation of Rac-(2S,3S)-5-allyl-6-hydroxy-2-(3,4-dimethoxypehnyl)-3-methyl-2,3-dihydrobenzofuran A solution of 3,4-dimethoxycinnamyl allyloxyphenyl ether in diethylaniline (6 ml) was heated at 225° C. for 13 hours, cooled, and diluted with diehtyl ether (30 ml). The solution was washed with 2N HCl and water, dried, and evaporated to a residue, which was purified by flash column chromatography on silica gel using hexane-ethyl acetate (4:1, v/v) as the eluant. The crude product was isolated as a crystalline mass (1.3 g, 43%), and was used for oxidation without further purification. A portion of this material was fractionated by HPLC to give pure Rac-(2S,3S)-5-allyl-6-hydroxy-2-(3,4-dimethoxypehnyl)-3-methyl-2,3-dihydrobenzofuran, m.p. 98°–99° C.; NMR (CDCl$_3$): δ1.39 (d, J=7.0 Hz, CH$_3$), 3.40 (d, J=5.5 Hz, CH$_2$CH=CH$_2$), 3.40 (m, H-3), 3.91, 3.92 (s, s, 2 OCH$_3$), 4.95 (s, OH), 5.10 (d, J=9.0 Hz, H-2), 5.17–5.26 (m, CH$_2$CH=CH$_2$), 6.60 (m, CH$_2$CH=CH$_2$), 6.44 (s, H-7), 6.90–7.02 (m, ArH).

Anal. Calc. for C$_{20}$H$_{22}$O$_4$: C, 73.60; H, 6.79. Found: C, 73.38; H, 6.73.

Step F: Preparation of 5-Allyl-2-(3,4-dimethoxyphenyl)-3-acetoxy-3-methyl-2,3,3a,6-tetrahydro-6-oxobenzofuran and related compounds Lead tetraacetate (275 mg, 0.6 mmol) was added to a solution of Rac-(2S,3S)-5-allyl-6-hydroxy-2-(3,4-dimethoxypehnyl)-3-methyl-2,3-dihydrobenzofuran (100 mg, 0.3 mmol) in dry methanol (10 ml), and the mixture was stirred at room temperature for 1.5 hours and evaporated to dryness. The products were extracted with dichloromethane and separated by flash column chromatography on silica gel (hexane-ethyl acetate, 4:1 to 2:1, v/v) followed by HPLC (silica gel; hexane-tetrahydrofuran, 4:1, v/v). The first eluted compound is rac-denudatin B (9.1 mg), NMR (CDCl$_3$): δ1.15 (d, J=7.0 Hz, CH$_3$), 2.21 (m, H-3), 3.16 (s, OCH$_3$), 3.19 (m, CH$_2$CH=CH$_2$), 3.92 (s, 2ArOCH$_3$), 5.12–5.21 (m, CH$_2$CH=CH$_2$), 5.38 (d, J=9.5 Hz, H-2), 5.86 (s, H-7), 5.91 (m, CH$_2$CH=CH$_2$), 6.30 (t, J=1.5 Hz, H-4), 6.83–6.92 (m, ArH). The second spot was identified as rac-kadsurenone (6.2 mg), NMR (CDCl$_3$): 1.12 (d, J=7.0 Hz, CH$_3$), 2.69 (q, d, J=7.0., 1.5 Hz, H-3), 3.04 (s, OCH$_3$), 3.15 (d, J=8.0 Hz, CH$_2$CH=CH$_2$), 3.89, 3.90 (s, s, 2ArOCH$_3$), 5.11 (d, t, J=13, 1.5 Hz, CH$_2$CH=CH$_2$), 5.12 (d, t, J=17, 2 Hz, CH$_2$CH=CH$_2$), 5.24 (s, H-2), 5.85 (m, CH$_2$CH=CH$_2$), 5.89 (s, H-7), 6.22 (t, J=1.5 Hz, H-4), 6.86 (d, J=8.5 Hz, H-5'), 6.90 (d, d, J=8.5, 2 Hz, H-6'), 7.02 (d, J=2.0 Hz, H-2'). The epimeric acetates (24.4 mg, about 1:1 mixture) were separated by HPLC into two isomers: the β-isomers, 5-allyl-2-(3,4-dimethoxyphenyl)-3a,β-acetoxy-3-methyl-2,3,3a,6-tetrahydro-6-oxobenzofuran. (CDCl$_3$): δ1.32 (d, J=7.0 Hz, CH$_3$), 2.14 (s, OAc), 2.58 (d, J=7.5 Hz, CH$_2$CH=CH$_2$), 3.08 (m, H-3), 3.94, 3.95 (s, s, 2ArOCH$_3$), 5.07 (d, J=8.5 Hz, H-2), 5.10–5.21 (m, CH$_2$CH=CH$_2$), 5.73 (s, H-7), 5.81 (m, CH$_2$CH=CH$_2$), 6.13 (d, J=2.5 Hz, H-4), 6.94 (ArH); and the α-isomer, 5-allyl-2-(3,4-dimethoxyphenyl)-3a,α-acetoxy-3-methyl-2,3,3a,6-tetrahydro-6-oxobenzo-furan. NMR (CDCl$_3$): δ1.34 (d, J=7.0 Hz, CH$_3$), 2.13 (s, OAc), 2.59 (d, J=7.5 Hz, CH$_2$CH=CH$_2$), 3.07 (m, H-3), 3.94, 3.95 (s, s, 2OCH$_3$), 5.11 (d, J=7.5 Hz, H-2), 5.10–5.20 (m, CH$_2$CH=CH$_2$), 5.75 (s, H-7), 5.79 (m, CH$_2$CH=CH$_2$), 6.14 (d, J=2.5 Hz, H-4), 6.91–6.96 (m, ArH).

Rsolution of the product was accomplished by a Chiralpak column of −20° C. using hexane-2-propanol (9:1, v/v) as a liquid phase.

EXAMPLE 2

3a-Methoxy-3-(3,4,5-trimethoxyphenyl)-5-propyl-2,3,3a,6-tetrahydro-6-oxobenzofuran Step A: Preparation of ω-(3-Allyloxyphenoxy)-3,4,5-trimethoxyacetophenone Potassium carbonate (13.3 g, 0.096 mol) was added to a solution of 3-allyoxyphenol (12 g, 0.08 mol) and 3,4,5-trimethoxyphenacylbromide (21.9 g, 0.096 mol) in acetone (250 ml), and the mixture was heated under reflux for 8 hours. It was filtered and the filtrate was evaporated to a residue, which was purified by HPLC (hexane-ethyl acetate; 2:1, v/v). The title compound was isolated as a crystalline mass; recrystallization from diethyl ether-petroleum ether gave pure ω-(3-allyloxyphenoxy)-3,4,5-trimethoxyacetophenone (8.6 g, 36%), m.p. 64°–65° C.

Step B: Preparation of 5-Allyl-6-hydroxy-3-(3,4,5-trimethoxyphenyl)benzofuran

A solution of ω-(3-allyloxyphenoxy)-3,4,5-trimethoxyacetophenone (3 g) in diethylaniline (3 g) was heated in a sealed tube at 235° C. for 5 hours cooled, and put on a column of silica gel to give 540 mg of 5-allyl-6-hydroxy-3-(3,4,5-trimethoxyphenyl)benzofuran. In addition, the corresponding 5-allyl-4-hydroxy isomer and the 7-allyl-6-hydroxy derivative were also isolated.

Step C: Preparation of 6-Hydroxy-3-(3,4,5-trimethoxyphenyl)-5-propyl-2,3-dihydrobenzofuran A solution of 5-allyl-6-hydroxy-3-(3,4,5-trimethoxyphenyl)benzofuran (130 mg) in glacial acetic acid (1 ml) containing 10% palladium-on-charcoal (50 mg) was hydrogenated for 2.5 h. The mixture was filtered and the filtrate was evaporated to give 6-hydroxy-3-(3,4,5-trimethoxyphenyl)-5-propyl-2,3-dihydrobenzofuran (90 mg).

Step D: Preparation of 3a-Methoxy-3-(3,4,5-trimethoxyphenyl)-5-propyl-2,3,3a,6-tetrahydro-6-oxo-benzofuran Lead tetraacetate (200 mg) was added to a solution of 6-hydroxy-3-(3,4,5-trimethoxyphenyl)-5-propyl-2,3-dihydrobenzofuran (100 mg) in dry methanol (10 ml), and the mixture was stirred at room temperature for 1 hour. The solution was evaporated to a residue, which was put on a flash column of silica gel and eluted with hexane-ethyl acetate (4:1, v/v). The title compound was isolated as a mixture of epimers.

EXAMPLE 3

3a-Methoxy-2-(3,4,5-trimethoxyphenyl)-5-propyl-2,3,3a,6-tetrahydro-6-oxo-benzofuran Step A: Preparation of 6-Hydroxy-3-(3,4,5-trimethoxyphenyl)-5-propylbenzofuran A solution of 5-allyl-6-hydroxy-3-(3,4,5-trimethoxyphenyl)benzofuran (300 mg) in ethyl acetate (2 ml) containing 5% palladium-on-charcoal was hydrogenated for 20 minutes. The mixture was filtered and the filtrate was evaporated to give 6-Hydroxy-3-(3,4,5-trimethoxyphenyl)-5-propylbenzofuran.

Step B: Preparation of 6-Hydroxy-2-(3,4,5-trimethoxyphenyl)-5-propylbenzofuran

Compound 6-hydroxy-3-(3,4,5-trimethoxyphenyl)-5-propylbenzofuran (1 g) was heated with stirring, with polyphoric acid at 130° C. for 20 minutes. It was cooled and the mixture was partitioned between diethyl ether and water. The organic layer was dried and evaporated to a residue, which was put on a flash column of silica gel and eluted with hexane-ethyl acetate (4:1, v/v). In addition to the product 6-Hydroxy-2-(3,4,5-trimethoxyphenyl)-5-propylbenzofuran (200 mg).

Step C: Preparation of 6-Hydroxy-2-(3,4,5-trimethoxyphenyl)-5-propyl-2,3-dihydrobenzofuran A solution of 6-Hydroxy-2-(3,4,5-trimethoxyphenyl)-5-propylbenzofuran (200 mg) in glacial acetic acid (1 ml) containing 10% palladium-on-charcoal was hydrogenated for 2.5 hours. The mixture was filtered and the filtrate was evaporated in vacuo to give 6-hydroxy-2-(3,4,5-trimethoxyphenyl)-5-propyl-2,3-dihydrobenzofuran (155 mg).

Step D: Preparation of 3a-Methoxy-2-(3,4,5-trimethoxyphenyl)-5-propyl-2,3,3a,6-tetrahydro-6-oxo-benzofuran Lead tetraacetate (200 mg) was added to a solution of 6-hydroxy-2-(3,4,5-trimethoxyphenol)-5-propyl-2,3-dihydrobenzofuran (100 mg) in dry methanol (10 ml), and the mixture was stirred at room temperature for 1 hour. It was concentrated to dryness, and the residue was partitioned between diethyl ether and water. The organic layer was dried and evaporated to residue, which was put on a flash column of silica gel and eluted with hexane-ethyl acetate (4:1, v/v). 3a-methoxy-2-(3,4,5-trimethoxyphenyl)-5-propyl-2,3,3a,6-tetrahydro-6-oxo-benzofuran was isolated as an epimeric mixture.

EXAMPLE 4

3a-acetoxy-2-(3,4-dimethoxyphenyl)-3-methyl-5-n-propyl-2,3,3a,6-tetrahydro-6-oxobenzofuran and related compounds Step A: Preparation of (2S,3S)-6-Hydroxy-2-(3,4-dimethoxyphenyl)-3-methyl-5-propyl-2,3-dihydrobenzofuran A solution of Rac-(2S,3S)-5-allyl-6-hydroxy-2-(3,4-dimethoxyphenyl)-3-methyl-2,3-dihydrobenzofuran (1.28 g) in ethyl acetate (30 ml) containing 10% palladium-on-charcoal (40 mg) was hydrogenated at 20 p.s.i. for 2 hours. The mixture was filtered and the filtrate was evaporated to give (2S,3S)-6-Hydroxy-2-(3,4-dimethoxyphenyl)-3-methyl-5-propyl-2,3-dihydrobenzofuran (1.2 g); n.m.r. (CDCl$_3$): δ0.99 (t, CH$_2$CH$_2$CH$_3$), 1.37 (d, CH$_3$—3), 1.65 (m, CH$_2$CH$_2$CH$_3$), 2.55 (t, CH$_2$CH$_2$CH$_3$), 3.38 (m, H-3), 3.90, 3.91 (s, s, 2OCH$_3$), 4.69 (b, OH), 5.07 (d, J 9.0 Hz, H-2), 6.06–7.01 (Ar—H), 6.38 (s, H-7).

Step B: Preparation of 3a-acetoxy-2-(3,4-dimethoxyphenyl)-3-methyl-5-n-propyl-2,3,3a,6-tetrahydro-6-oxobenzofuran and related compounds Lead tetraacetate (275 mg, 0.6 mmol) was added to a solution of (2S,3S)-6-Hydroxy-2-(3,4-dimethoxyphenyl)-3-methyl-5-propyl-2,3-dihydrobenzofuran (100 mg), 0.3 mmol) in dry methanol (10 ml), and the mixture was stirred at room temperature for 1.5 hours and evaporated to dryness. The products were extracted with dichloromethane and separated by flash chromatography on silica gel (hexane-ethyl acetate, 4:1 to 2:1, v/v) followed by HPLIC (silica gel; hexane-tetrahydrofuran, 4:1, v/v). The first eluted compound was (2S,3S,3aR)-2-(3,4-dimethoxyphenyl)-3a-methoxy-3-methyl-5-n-propyl-2,3,3a,6-tetrahydro-6-oxo-benzofuran (9 mg), n.m.r. (CDCl$_3$): δ0.99 (t, J 7.5 Hz, CH$_2$CH$_2$CH$_3$), 1.16 (d, J 7.0 Hz, CH$_3$—3), 1.55 (m, CH$_2$CH$_2$CH$_3$), 2.20 (m, H-3), 2.39 (m, CH$_2$CH$_2$CH$_3$), 3.16 (s, OCH$_3$), 3.92 (s, s 2A-r—OCH$_3$), 5.38 (d, J 9.5 Hz, H-2), 5.84 (s, H-7), 6.27 (s, H-4), 6.84–6.93 (Ar—H). The second spot was identified as (2S,3S,3aS)-2-(3,4-dimethoxyphenyl)-3a-methoxy-3-methyl-5-n-propyl-2,3,3a,6-tetrahydro-6-oxo-benzofuran (6 mg), n.m.r. (CDCl$_3$): 0.96 (t, J 7.5 Hz, CH$_2$CH$_2$CH$_3$), 1.15 (d, J 7.0 Hz, CH$_3$—3), 1.53 (m, CH$_2$CH$_2$CH$_3$), 2.38 (m, CH$_2$CH$_2$CH$_3$), 2.72 (m, H-3), 3.05 (s, OCH$_3$), 3.90, 3.91 (s, s, 2OCH$_3$), 5.26 (s, H-2) 5.92 (s, H-7), 6.22 (s, H-4), 6.88–7.06 (m, Ar—H). The corresponding epimeric acetates (24 mg, about 1:1 mixture) were separated by HPLC: (2S,3S,3aR)-3a-Acetoxy-2-(3,4-dimethoxyphenyl)-3-methyl-5-n-propyl-2,3,3a,6-tetrahydro-6-oxo-benzofuran n.m.r. (CDCl$_3$): 0.93 (t, J 7.0 Hz, CH$_2$CH$_2$CH$_3$), 1.34 (d, J 7.0 Hz, CH$_3$—3), 1.40 (m, CH$_2$CH$_2$CH$_3$), 1.83 (m, CH$_2$CH$_2$CH$_3$), 2.13 (s, OAc), 3.05 (m, H-3), 3.94, 3.95 (s, s, 2OCH$_3$), 5.08 (d, J 8.2 Hz, H-2), 5.73 (s, H-7), 6.15 (d, J 1.5 Hz, H-4), 6.88–6.99 (m, Ar—H); and (2S,3S,3aS)-3a-Acetoxy-2-(3,4-dimethoxyphenyl)-3-methyl-5-n-propyl-2,3,3a,6-tetrahydro-6-oxo-benzofuran, n.m.r. (CDCl$_3$): δ0.92 (t, J 7.02 Hz, CH$_2$CH$_2$CH$_3$), 1.34 (d, J 7.0 Hz, CH$_3$—3), 1.38 (m, CH$_2$CH$_2$CH$_3$), 1.83 (m, CH$_2$CH$_2$CH$_3$), 2.13 (s, OAc), 3.07 (m, H-3), 3.94 (s, 2OCH$_3$), 5.10 (d, J 7.6 Hz, H-2), 5.73 (s, H-7), 6.15 (d, J 1.5 Hz, H-4), 6.84–6.94 (m, Ar—H).

EXAMPLE 5

(2S,3S,3aS)-2-(3,4-Dimethoxyphenyl)-3a-methoxy-3-methyl-5-n-propyl-2,3,3a,6-tetrahydro-6-methoxyiminobenzofuran (2S,3S,3aS)-2-(3,4-Dimethoxyphenyl)-3a-methoxy-3-methyl-5-n-propyl-2,3,3a,6-tetrahydro-6-methoxyiminobenzofuran was prepared from (2S,3S,3aS)-2-(3,4-dimethoxyphenyl)-3a-methoxy-3-methyl-5-n-propyl-2,3,3a,6-tetrahydro-6-oxobenzofuran and methoxylamine hydrochloride in pyridine at room temperature for 3 days. The product was purified by flash column chromatography on silica gel (hexane-ethyl acetate, 9:1, v/v) followed by HPLC to afford (2S,3S,3aS)-2-(3,4-dimethoxyphenyl)-3a-methoxy-3-methyl-5-n-propyl-2,3,3a,6-tetrahydro-6-methoxyiminobenzofuran, n.m.r. (CDCl$_3$): δ0.98 (t, J 7.5 Hz, CH$_2$CH$_2$CH$_3$), 1.11 (d, CH$_3$—3), 1.64 (m, CH$_2$CH$_2$CH$_3$), 2.52 (m, CH$_2$CH$_2$CH$_3$), 3.0 (s, OCH$_3$), 3.84 (s, Ar—OCH$_3$), 4.04 (s, NOCH$_3$), 5.07 (s, H-2), 5.72 (s, H-7) 6.48 (s, H-4), 6.87–7.12 (m, Ar—H).

EXAMPLE 6

(2S,3S,3aS)-5-Allyl-2-(3,4-dimethoxyphenyl)-3a-ethoxy-3-methyl-2,3,3a,6-tetrahydro-6-oxo-benzofuran Following substantially the same procedures as described in Example 2, Step E, except that ethanol was used in place of methanol there were obtained two products: (2S,3S,3aR)-5-allyl-2-(3,4-dimethoxyphenyl)-3a-ethoxy-3-methyl-2,3,3a,6-tetrahydro-6-oxo-benzofuran, n.m.r. (CDCl$_3$): δ1.15 (t, J 7.0 Hz, OCH$_2$CH$_3$), 1.15 (d, J 7.0 Hz, CH$_3$—3), 2.17 (m, H-3), 3.17 (m, CH$_2$CH=CH$_2$), 3.33 (q, OCH$_2$CH$_3$), 3.92 (s, 2OCH$_3$), 5.10–5.22 (m, CH$_2$CH=CH$_2$), 5.41 (d, J 9.5 Hz, H-2), 5.82 (s, H-7), 6.33 (t, J 1.5 Hz, H-4), 6.82–6.92 (m, Ar—H); and (2S,3S,3aS)-5-allyl-2-(3,4-dimethoxyphenyl)-3a-ethoxy-3-methyl-2,3,3a,6-tetrahydro-6-oxo-benzofuran, n.m.r. (CDCl$_3$): δ0.95 (t, J 7.0 Hz, OCH$_2$CH$_3$), 1.12 (d, J 7.5 Hz, CH$_3$—3), 2.76 (m, H-3), 3.15 (m, CH$_2$CH=CH$_2$), 3.28 (q, OCH$_2$CH$_3$), 3.92, 3.93 (s, s, 2OCH$_3$), 5.07–5.20 (m, CH$_2$CH=CH$_2$), 5.26 (s, H-2), 5.89 (s, H-7), 5.91 (m, CH₂C̲H̲=CH₂), 6.30 (s, H-4), 6.80–7.06 (m, Ar—H).

EXAMPLE 7

(2S,3S,3aS)-5-Allyl-2-(3,4,5-trimethoxyphenyl)-3a-methoxy-3-methyl-2,3,3a,6-tetrahydro-6-oxo-benzofuran Following substantially the same procedures of Example 1, Steps A to F, there were obtained the following intermediates and products:

3,4,5-Trimethoxycinnamyl allyloxyphenyl ether, in 16.2% yield from 3-allyloxyphenol and 3,4,5-trimethoxycinnamyl alcohol. Mass spectrum: m/e 356 (M+.);

Rac-(2S,3S)-5-allyl-6-hydroxy-2-(3,4,5-trimethoxyphenyl)-3-methyl-2,3-dihydrobenzofuran in 24% yield, m.p. 166°–167° C.; mass spec. m/e 356 (M+.)

Anal. Calc. for $C_{21}H_{24}O_5$: C, 70.77; H, 6.79. Found: C, 70.35; H, 6.74;

(2S,3S,3aS)-5-Allyl-2-(3,4,5-trimethoxyphenyl)-3a-methoxy-3-methyl-2,3,3a,6-tetrahydro-6-oxo-benzofuran, n.m.r. spectrum is in accord with the structure and indicating a mixture of epimers.

What is claimed is:

1. A compound which is: (2S,3S,3aS)-2-(3,4-dimethoxyphenyl)-3a-methoxy-3-methyl-5-n-propyl-2,3,3a,6-tetrahydro-6-methoxyiminobenzofuran.

* * * * *